United States Patent [19]

Morozumi et al.

[11] Patent Number: 5,939,543
[45] Date of Patent: Aug. 17, 1999

[54] STABLE SOLID 2-OCTYNYL ADENOSINE AND PROCESS FOR PRODUCING THE SAME

[75] Inventors: Manami Morozumi; Masao Kumagai, both of Choshi; Toyofumi Yamaguchi, Hachioji, all of Japan

[73] Assignee: Yamasa Shoyu Kabushiki Kaisha, Japan

[21] Appl. No.: 07/833,718

[22] Filed: Feb. 11, 1992

[30] Foreign Application Priority Data

Feb. 12, 1991 [JP] Japan .................................. 3-040894

[51] Int. Cl.$^6$ .................................. C07H 19/167
[52] U.S. Cl. .................. 536/27.63; 536/27.6; 536/27.61; 536/27.62; 514/26
[58] Field of Search ................. 514/46; 536/24, 536/27, 63

[56] References Cited

U.S. PATENT DOCUMENTS 4,956,345 9/1990 Miyasaka et al. ........................ 514/46

FOREIGN PATENT DOCUMENTS

A-0444196 4/1991 European Pat. Off. .
A-0429681 5/1992 European Pat. Off. .
A-9005526 5/1990 Japan .

OTHER PUBLICATIONS

"Aldrich Catalog/Handbook of Fine Chemicals," Aldrich Chemical Company, Milwaukee, WI, 1984–1985, p. 1358.
Matsuda et al. (I), *Nucl. Acids Res. Symp. Ser.,* 16, 97–100 (1985).
Matsuda et al.(II), *Nucl. Acids Res. Symp. Ser.,* 12, 5–8 (1983).
Matsuda et al.(III), *Chem. Pharm Bull.*, 33(4), 1766–1769 (1985).
Weygand et al., "Preparative Organic Chemistry," Hilgetag et al. eds., John Wiley and Sons, New York, 1972, see pp. 1096–1098, 1111–1121, 1127.

*Primary Examiner*—Marian C Knode
*Assistant Examiner*—L. Eric Crane
*Attorney, Agent, or Firm*—Wenderoth, Lind & Ponack, L.L.P.

[57] ABSTRACT

The present invention provides two kinds of solid 2-octynyl adenosine products with novel properties which are stabilized with respect to temperature or temperature and humidity, one being solid 2-octynyl adenosine having a moisture content of not more than 3%, and the other being solid 2-octynyl adenosine deposited from an anhydrous alcoholic solution or hydrous alcoholic solution of 2-octynyl adenosine, said hydrous alcoholic solution having a water content of less than 1%.

24 Claims, 12 Drawing Sheets

STABLE SOLID 2-OCTYNYL ADENOSINE AND PROCESS FOR PRODUCING THE SAME

BACKGROUND OF THE INVENTION

The present invention relates to solid 2-octynyl adenosine with novel properties which does not decompose at a high temperature or at a high temperature and under a high humidity and thus which is stabilized with respect to temperature or temperature and humidity.

2-Octynyl adenosine is a compound wherein an octynyl group is introduced into the 2-position of adenosine through a carbon-carbon bond, and has an antihypertensive activity. The development of 2-octynyl adenosine as medicines is anticipated. (See Nucleic Acids Research Symposium Series No.12, pp.5–8 (1983), Chem. Pharm. Bull., 33, pp.1766–1769 (1985), Nucleic Acids Research Symposium Series No.16, pp.97–100 (1985), Nucleosides & Nucleotides, 6 (1&2), pp.85–94 (1987), Japanese Patent Laid-Open Publication No. 99395/1987, Japanese Patent Laid-Open Publication No. 99330/1987, and U.S. Pat. No. 4,956,345.)

Heretofore, 2-octynyl adenosine has been generally produced in the final step in the form of a monohydrate crystal by gradually crystallizing from a methanol/water solvent mixture (ordinarily methanol containing 10 to 50% water) or in amorphous form by rapidly depositing from a methanol/water solvent mixture. However, it is well known that the water content of the thus obtained compound is ordinarily 4.6% or higher so that the compound is unstable with respect to temperature and humidity. For example, according to the results of a severe test for evaluation of its long-term storage stability (stored for 3 months at 40° C. under a relative humidity of 75%), the percentage of the remaining crystalline 2-octynyl adenosine monohydrate or amorphous 2-octynyl adenosine is about 70%. (See WO90/15812.) Therefore, it is impossible to enjoy such a "scale" merit that 2-octynyl adenosine produced on a large scale is stored until it is needed, whereby 2-octynyl adenosine must be produced on a small scale when needed. When the production of a large amount of 2-octynyl adenosine is required, a special apparatus capable of controlling temperature and/or humidity has to be employed in order to store the 2-octynyl adenosine.

Accordingly, if 2-octynyl adenosine stabilized with respect to temperature and/or humidity is obtained, great industrial benefits can be achieved.

It is therefore an object of the present invention to provide 2-octynyl adenosine with novel properties which is stabilized with respect to either temperature or humidity, preferably with respect to both factors.

SUMMARY OF THE INVENTION

We have now found that novel solid 2-octynyl adenosine having properties different from those of the prior art crystalline 2-octynyl adenosine monohydrate or amorphous 2-octynyl adenosine can be successfully produced and that this novel solid 2-octynyl adenosine has remarkable storage stability. On the basis of this finding, we have arrived at the present invention.

The present invention provides solid 2-octynyl adenosine having a water content of not more than 3% (hereinafter sometimes referred to as "low-moisture 2-octynyl adenosine") and a process for producing the same.

The present invention also provides solid 2-octynyl adenosine deposited from an anhydrous alcoholic solution or hydrous alcoholic solution of 2-octynyl adenosine wherein said hydrous alcoholic solution has a water content of less than 1% (hereinafter sometimes referred to as "alcohol-deposited 2-octynyl adenosine") and a process for producing the same.

DETAILED DESCRIPTION OF THE INVENTION

Starting materials for producing the stabilized solid 2-octynyl adenosine of the present invention may be either solid 2-octynyl adenosine produced by a known method (a crystalline 2-octynyl adenosine monohydrate or amorphous 2-octynyl adenosine) or liquid 2-octynyl adenosine prior to crystallization or deposition of the crystalline or amorphous compound described above.

Production of Low-Moisture 2-Octynyl Adenosine

The low-moisture 2-octynyl adenosine can be produced by dehydrating the crystalline 2-octynyl adenosine monohydrate or amorphous 2-octynyl adenosine until its water content is reduced to not more than 3%, preferably not more than 1%.

The dehydration methods and conditions are not particularly limited. The starting 2-octynyl adenosine may be dehydrated by any conventional methods such as vacuum drying, air drying and heating under conditions such that 2-octynyl adenosine is not decomposed. The vacuum drying method is particularly preferred wherein dehydration is carried out under reduced pressure of not more than 20 mmHg, preferably not more than 10 mmHg at a temperature lower than the melting point of 2-octynyl adenosine, preferably from 50° C. to 90° C.

Even if the thus obtained low-moisture 2-octynyl adenosine is stored at a high temperature, it does not decompose and is stable with respect to temperature. The low-moisture 2-octynyl adenosine is still unstable with respect to humidity, and therefore it is preferred that the low-moisture 2-octynyl adenosine be stored in a sealable container in the presence of a desiccating agent such as silica gel ordinarily under a relative humidity of not more than 30%.

Properties of Low-Moisture 2-Octynyl Adenosine

The properties of low-moisture 2-octynyl adenosine will be described hereinbelow with reference to 2-octynyl adenosine having a water content of 0.9% as a typical example.

(a) Powder X-Ray Diffraction Spectrum

Figure 1:
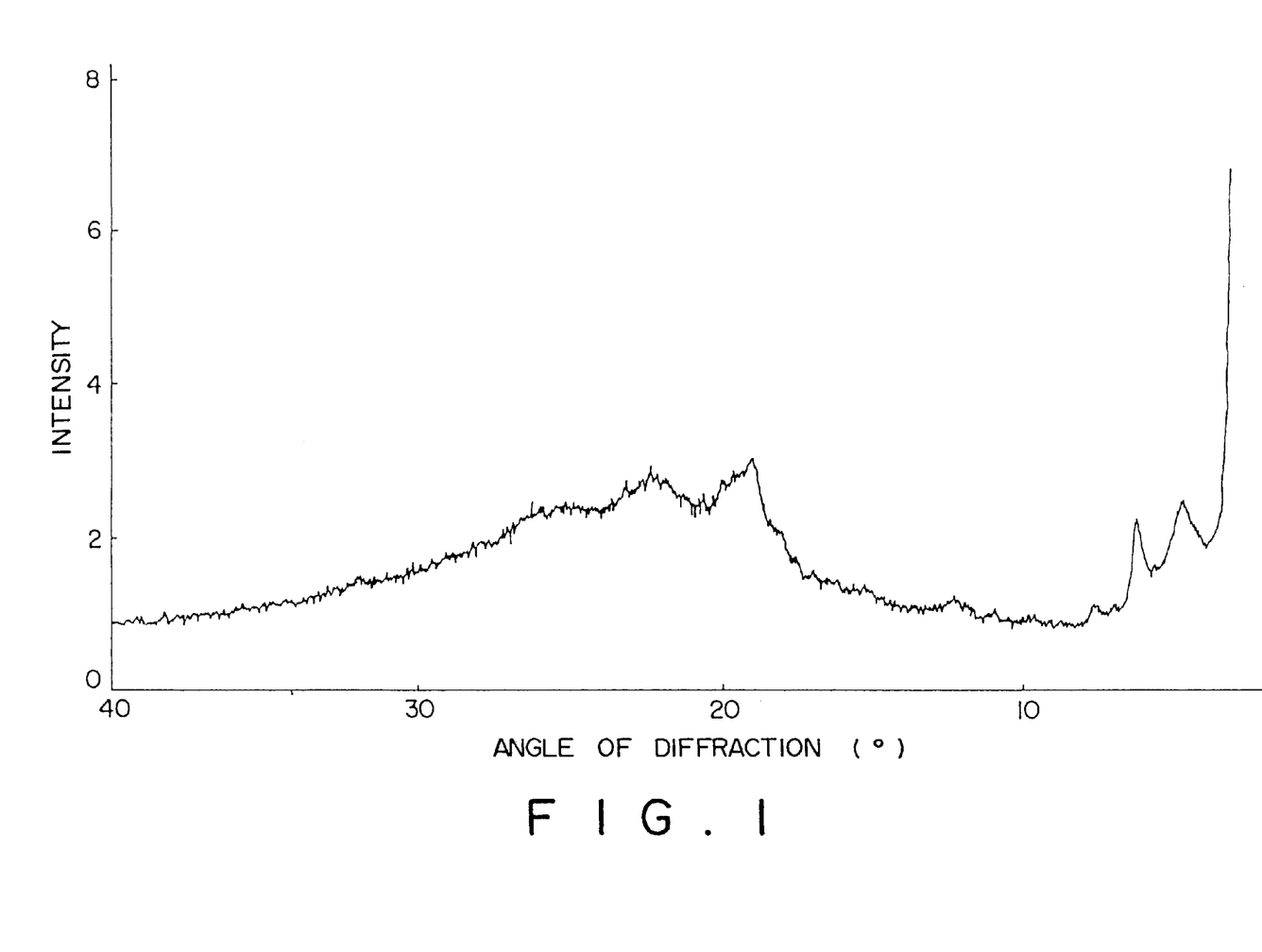
FIG. 1 is a graph showing a powder X-ray diffraction spectrum of the low-moisture 2-octynyl adenosine of the present invention.

Measurements were carried out under the following conditions by means of X-ray diffractometer Model PW1710-1729 manufactured by Philips Company. The results are shown in FIG. 1.

Figure 2:
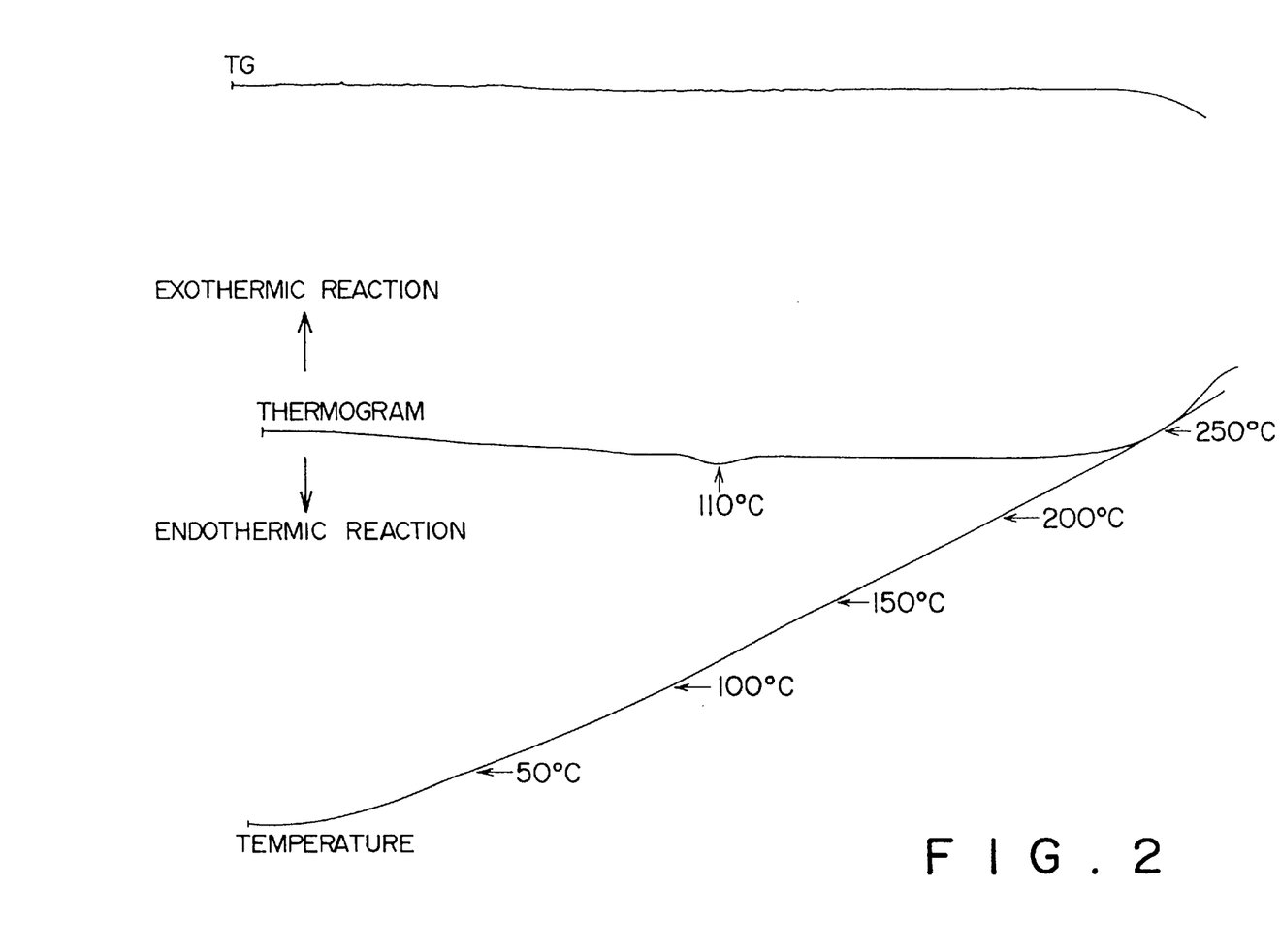
FIG. 2 is a graph showing a thermogram of the low-moisture 2-octynyl adenosine of the present invention.

Measurement Conditions
  Target: Cu long fine-focus (L.F.F.PW2273/20)
  X-ray intensity: 40 KVp, 20 mA
  Detector: PC (PW1711/10)
  Monochromator: Graphite Type (PW1752/00)
  Scanning speed: 1°/min.
  Scanning range: 3° to 60°
  Diverging slit: 1°
  Receptor slit: 0.2 mm
  Antiscattering slit: 1°
  Chart speed: 10 mm/min.
  Time constant: 2 seconds
  Chart full scale: 2 Kcps (b) Thermogram When differential thermoanalysis was carried out under the following conditions by means of thermogravimetric analyzer Model TGD-3000 manufactured by Shinku Rico K.K., an endothermic reaction was observed at 110° C (±1° C.) for the sample. The curve obtained is shown in FIG. 2. For all of 2-octynyl adenosine products having a water content of not more than 3%, an endothermic reaction as described above was observed at 110° C. (±1° C.).

Measurement Conditions
  Measurement temperature: room temperature to 350° C.
  Standard sample: α-Al$_2$O$_3$
  Sensitivity (full scale)
  Temperature: 500° C.
  Differential heat: ±100 μV
  Weight: 20 mg
  Temperature raising rate: 5° C./min.

(c) Infrared Absorption Spectrum

Figure 3:
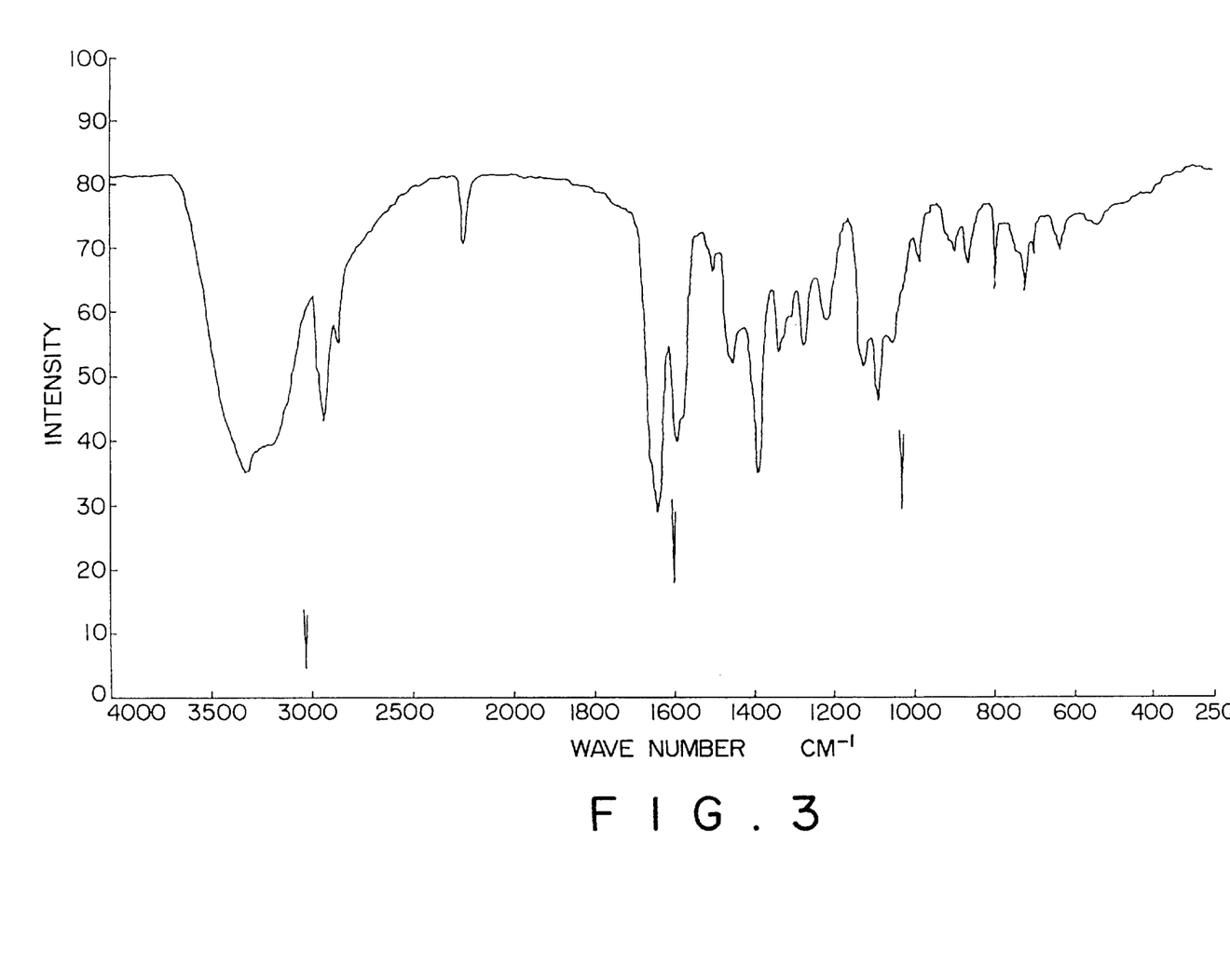
FIG. 3 is a graph showing an infrared absorption spectrum of the low-moisture 2-octynyl adenosine of the present invention.

The infrared absorption spectrum was measured by the KBr method by means of infrared spectrometer Model 260-50 manufactured by Hitachi Seisakusho K.K. The results are shown in FIG. 3. All of 2-octynyl adenosine products having a water content of not more than 3% showed substantially the same infrared absorption spectrum as that shown in FIG. 3.

(d) Stability

2-Octynyl adenosine products were hermetically sealed and stored for 10 and 20 days respectively at the storage temperatures shown in Table 1 at a relative humidity of about 30% to measure the percentage of the remaining 2-octynyl adenosine. The results are shown in Table 1. The results of the prior art monohydrate crystal are shown in Table 1 as control. As shown in Example 1, in the cases of all of 2-octynyl adenosine products having a water content of not more than 3%, their decomposition was inhibited even at a high temperature (e.g., 50° C.), and the products are stable with respect to temperature.

TABLE 1

| Product | Water Content (%) | Storage Temperature (° C.) | Percentage of the Remaining Product (%) | | |
|---|---|---|---|---|---|
| | | | At the Beginning of Storage | After 10 days | After 20 days |
| Product of the present invention | 0.9 | 5 | 100 | 100 | 100 |
| | | 25 | 100 | 100 | 99.9 |
| | | 50 | 100 | 99.0 | 97.7 |
| Prior art product (monohydrate crystal) | 4.6 | 5 | 99.9 | 95.3 | 84.4 |
| | | 25 | 99.9 | 90.6 | 75.2 |
| | | 50 | 99.9 | — | 68.3 |

Note: Each water content shown in Table 1 was measured by the Karl Fischer's method.

(e) Crystal Form

Figure 4:
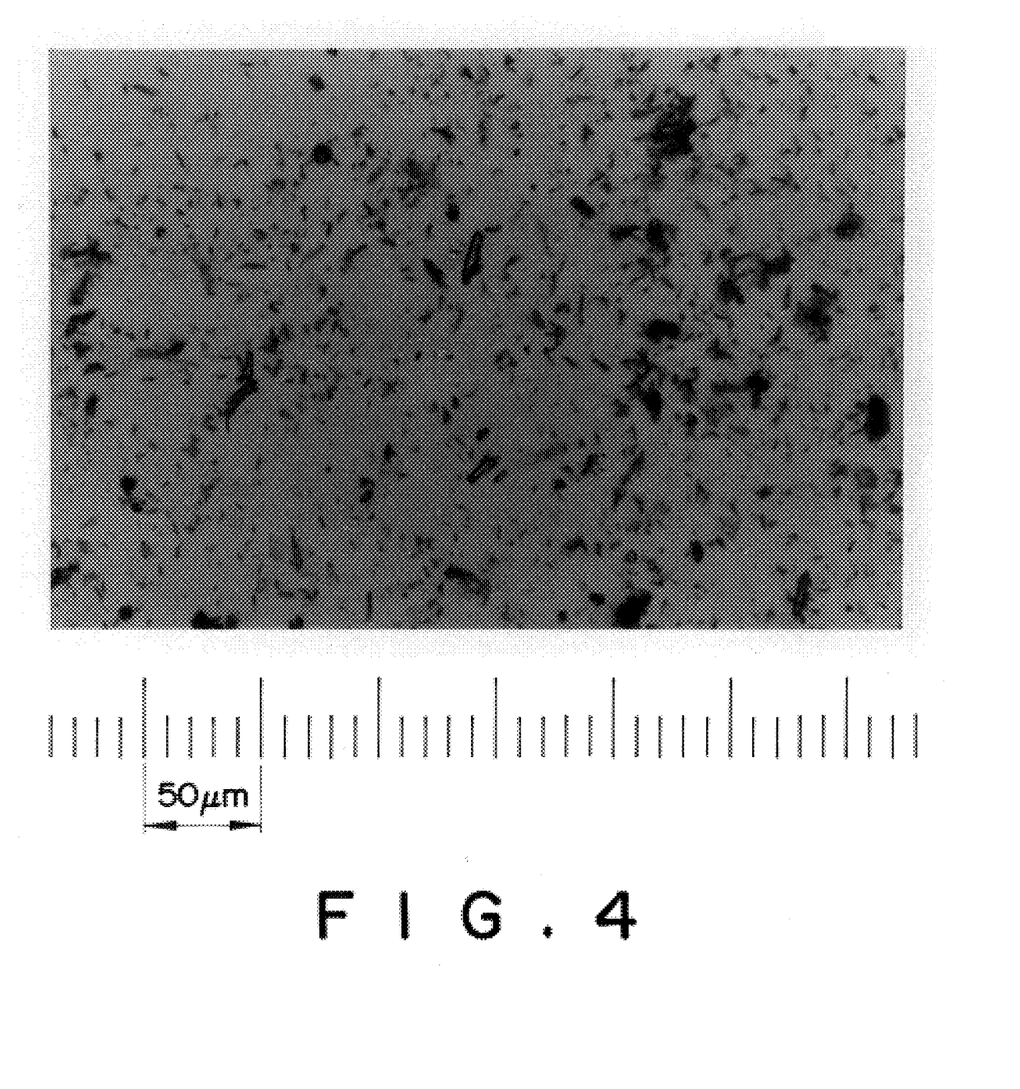
FIG. 4 is a photomicrograph showing the crystal form of the low-moisture 2-octynyl adenosine of the present invention (at a magnification of 330)

The crystal form was observed under biological microscope Model BH-2 manufactured by Olympus K.K. at a magnification of about 330. The results are shown in FIG. 4.

Production of Alcohol-Deposited 2-Octynyl Adenosine

The alcohol-deposited 2-octynyl adenosine can be produced by dehydrating crystalline 2-octynyl adenosine monohydrate or amorphous 2-octynyl adenosine so that its water content is reduced to not more than 3%, dissolving the dehydrated 2-octynyl adenosine in absolute alcohol or a hydrous alcohol containing less than 1% water with heating, and cooling the solution (by quenching or allowing to stand) to deposit a desired product.

Methods of dehydrating the crystalline 2-octynyl adenosine monohydrate or amorphous 2-octynyl adenosine (usually having a water content of at least 4.6%) are not particularly limited. The starting 2-octynyl adenosine may be dehydrated by any methods such as vacuum drying, air drying and heating. Further, the residue obtained by dissolving the crystalline 2-octynyl adenosine monohydrate or amorphous 2-octynyl adenosine in alcohols to obtain a solution and dehydrating the solution by azeotropic distillation may be used as a starting material.

The alcohols for dissolving the dehydrated 2-octynyl adenosine are not limited provided that they contain not more than 6 carbon atoms in the molecule (excluding methanol). Ethanol, propanol and butanol are particularly preferred. These alcohols may be either those containing a straight carbon chain or those containing a branched carbon chain. Alcohols containing a straight carbon chain are preferred for ease in depositing 2-octynyl adenosine. It is essential that alcohols containing less than 1% water, preferably absolute alcohol be used. If alcohols containing 1% or more water are used as a solvent, it will be difficult to obtain stabilized 2-octynyl adenosine.

Practical operations may be carried out by dissolving the dehydrated 2-octynyl adenosine as described above in the alcohol described above at a temperature of 30° C. to 90° C. so that the concentration of the 2-octynyl adenosine is of the order of 5 to 30% (W/V), preferably from 10 to 20% (W/V), and then cooling (quenching or gradually cooling) the resulting solution to a temperature of 10° C. to lower than 30° C. Thus, solid 2-octynyl adenosine stable with respect to temperature and humidity can be obtained.

The thus obtained alcohol-deposited 2-octynyl adenosine has a water content of less than 1%. Even after storage at a high temperature and a high humidity, its decomposition is inhibited and the 2-octynyl adenosine is stabilized with respect to temperature and humidity. If necessary, it can be further dried by any conventional methods such as vacuum drying, contained in a container (such as bottles, bags, cans and ampules) and stored until use. The 2-octynyl adenosine may be contained in the container in an open, closed, air-tight or sealed state. The open state is less desirable from the standpoint of maintaining storage stability.

Properties of Alcohol-Deposited 2-Octynyl Adenosine

The properties of alcohol-deposited 2-octynyl adenosine will be described hereinbelow with reference to solid 2-octynyl adenosine obtained by depositing from an anhydrous propanol solution of 2-octynyl adenosine as a typical example.

(a) Powder X-ray Diffraction Spectrum

Figure 5:
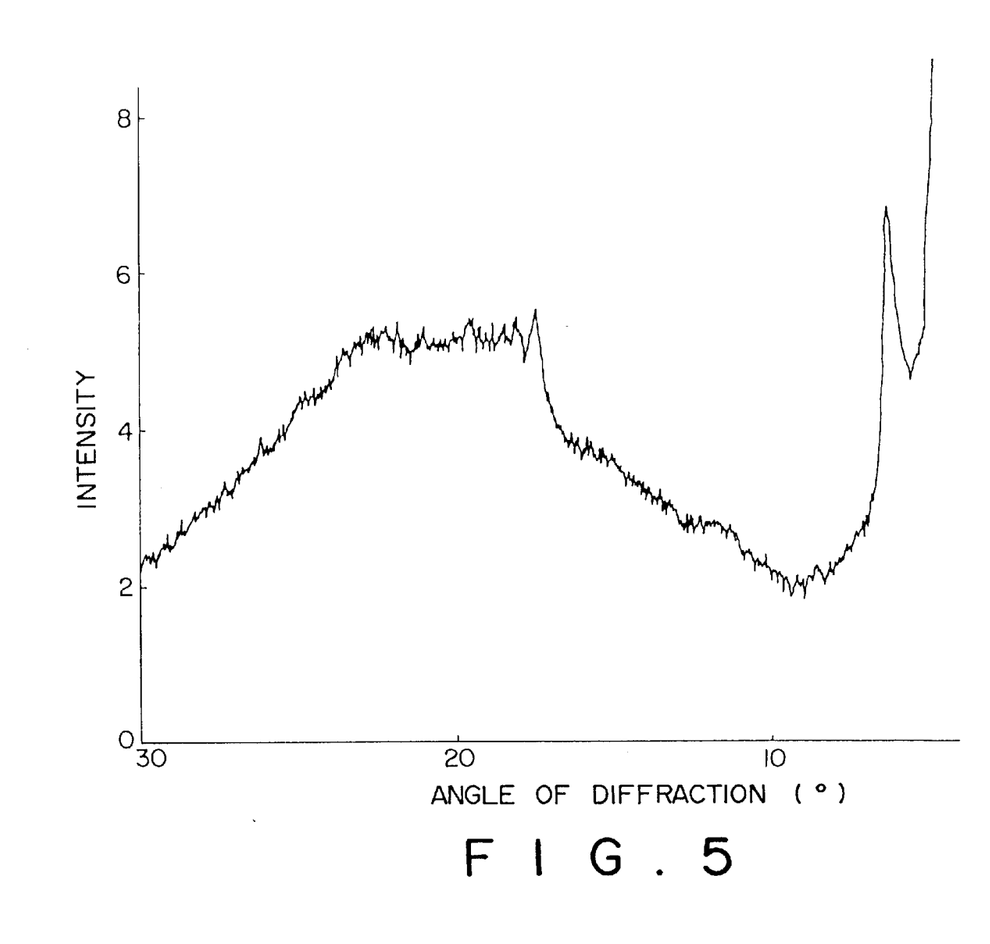
FIG. 5 is a graph showing a powder X-ray diffraction spectrum of the alcohol-deposited 2-octynyl adenosine of the present invention.

Measurements were carried out under the same conditions as in the case of the low-moisture 2-octynyl adenosine by means of X-ray diffractometer Model PW1710-1729 manufactured by Philips Company. The results are shown in FIG. 5. The powder X-ray diffraction spectra of solid 2-octynyl adenosine products obtained by depositing from solutions of 2-octynyl adenosine in anhydrous ethanol and butanol and solutions of 2-octynyl adenosine in hydrous ethanol, propanol and butanol containing less than 1% water are substantially identical with that shown in FIG. 5.

(b) Thermogram

Figure 6:
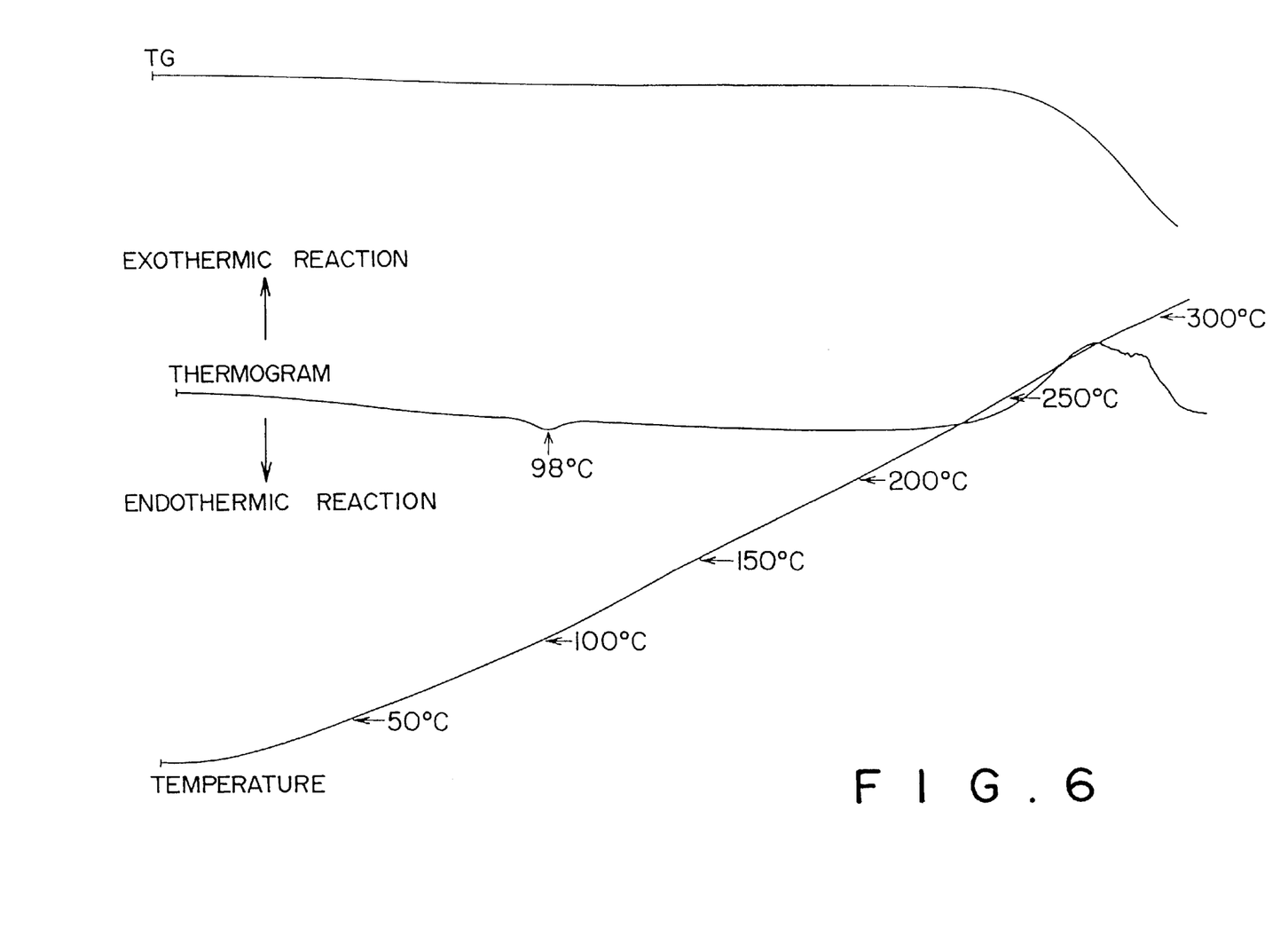
FIG. 6 is a graph showing a thermogram of the alcohol-deposited 2-octynyl adenosine of the present invention.

When differential thermoanalysis was carried out under the same conditions as in the case of the low-moisture 2-octynyl adenosine by means of thermogravimetric analyzer Model TGD-3000 manufactured by Shinku Rico K.K., an endothermic reaction was observed at 98° C. (±1° C.) for the sample. The curve obtained is shown in FIG. 6. For solid 2-octynyl adenosine products obtained by depositing from a solution of 2-octynyl adenosine in hydrous propanol containing less than 1% water, a solution of 2-octynyl adenosine in anhydrous ethanol or hydrous ethanol containing less than 1% water and a solution of 2-octynyl adenosine in anhydrous butanol or hydrous butanol containing less than 1% water, an endothermic reaction was observed at 98° C. (±1° C.), 99° C. (±1° C.) and 110 (±1° C.), respectively.

(c) Infrared Absorption Spectrum

Figure 7:
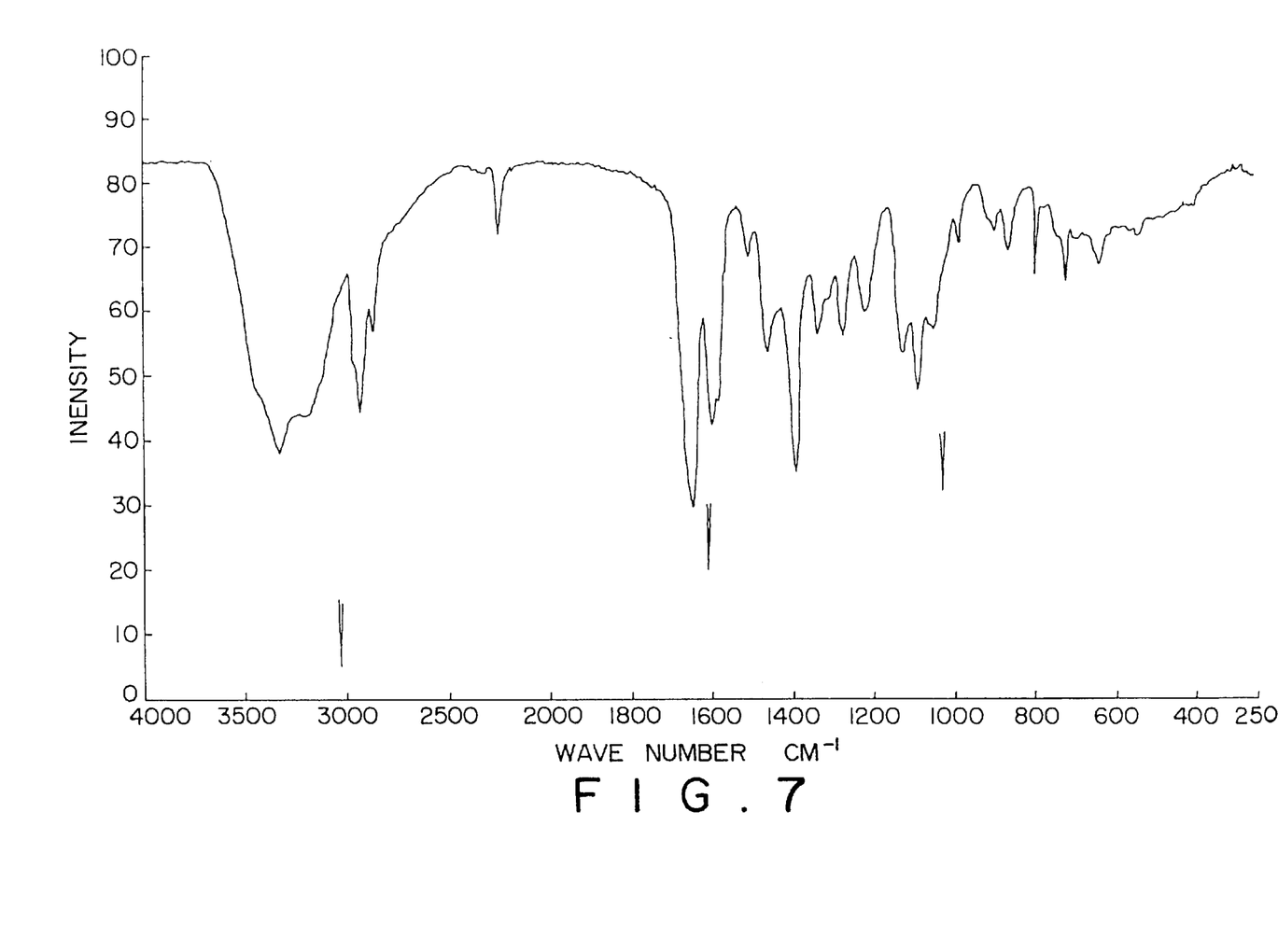
FIG. 7 is a graph showing an infrared absorption spectrum of the alcohol-deposited 2-octynyl adenosine of the present invention.

The infrared absorption spectra were measured by the KBr method by means of infrared spectrometer Model 260-50 manufactured by Hitachi Seisakusho K.K. The results are shown in FIG. 7. Infrared absorption spectra of solid 2-octynyl adenosine products obtained by depositing from a solution of 2-octynyl adenosine in hydrous propanol containing less than 1% water, a solution of 2-octynyl adenosine in anhydrous ethanol or hydrous ethanol containing less than 1% water, and a solution of 2-octynyl adenosine in anhydrous butanol or hydrous butanol containing less than 1% water are substantially identical with that shown in FIG. 7.

(d) Stability

Solid 2-octynyl adenosine products obtained by depositing from solutions of 2-octynyl adenosine in anhydrous alcohols (ethanol, n-propanol and n-butanol) were stored for 3 and 6 days under severe conditions of a temperature of 50° C. and a relative humidity of about 57% to measure the percentage of the remaining 2-octynyl adenosine. The results are shown in Table 2. The results of the prior art monohydrate crystal are shown in Table 1 as control. As shown in Example 2, 2-octynyl adenosine products obtained by depositing from solutions of 2-octynyl adenosine in hydrous alcohols containing less than 1% water did not decompose even after storage under similar conditions of a high temperature and a high humidity (e.g., 50° C., 57%). The products are stable with respect to temperature and humidity.

TABLE 2

| Product | Percentage of the Remaining Product (%) | | |
|---|---|---|---|
| | At the Beginning of Storage | After 3 days | After 6 days |
| Product of the present invention Solvent: | | | |
| Ethanol | 98.0 | — | 98.8 |
| n-Propanol | 99.8 | — | 99.4 |
| n-Butanol | 98.7 | 98.8 | 99.0 |
| Prior art product (monohydrate crystal) | 98.7 | 84.9 | 82.5 |

(e) Crystal Form

Figure 8:
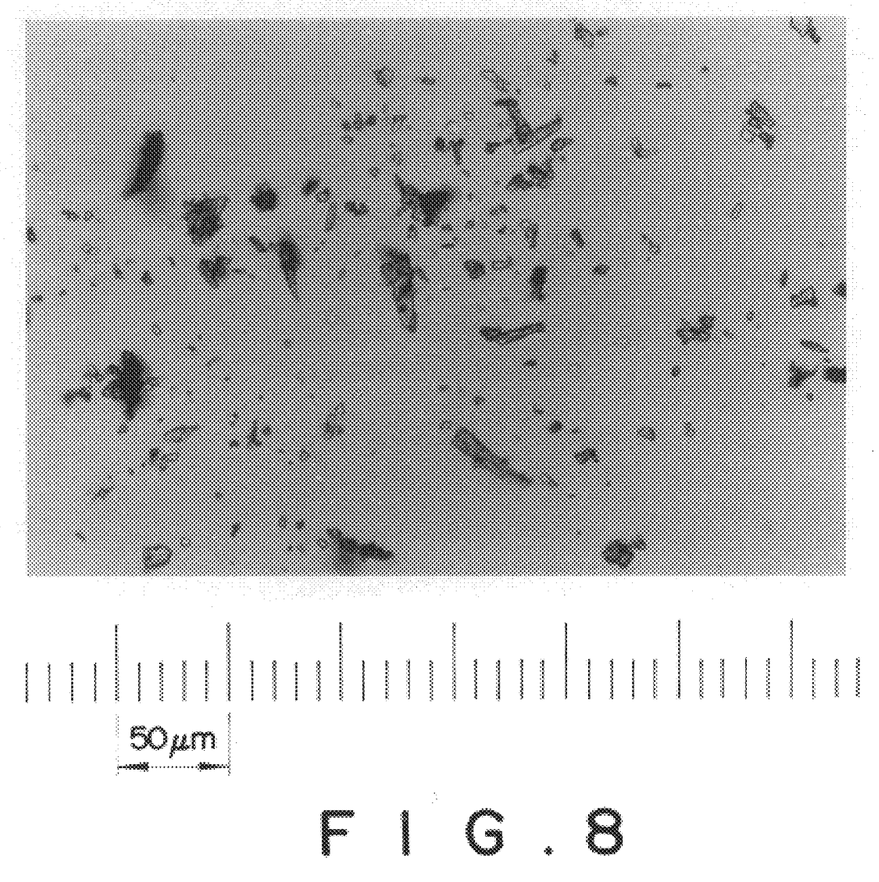
FIG. 8 is a photomicrograph showing the crystal form of the alcohol-deposited 2-octynyl adenosine of the present invention (at a magnification of 330)

The crystal form was observed under biological microscope Model BH-2 manufactured by Olympus K.K. at a magnification of about 330. The results are shown in FIG. 8.

As stated above, the low-moisture and alcohol-deposited 2-octynyl adenosine products of the present invention have by far higher stability as compared with the prior art crystalline 2-octynyl adenosine monohydrate and are extremely useful compounds capable of overcoming the drawbacks of the prior art crystalline 2-octynyl adenosine monohydrate.

Because the low-moisture and alcohol-deposited 2-octynyl adenosine products of the present invention are apparently different from the prior art crystalline 2-octynyl adenosine monohydrate as described hereinafter also from the standpoints of properties other than stability, particularly in respect of powder X-ray diffraction spectra, thermogram and crystal form, both solid 2-octynyl adenosine products of the present invention can be said to be novel 2-octynyl adenosines.

Figure 9:
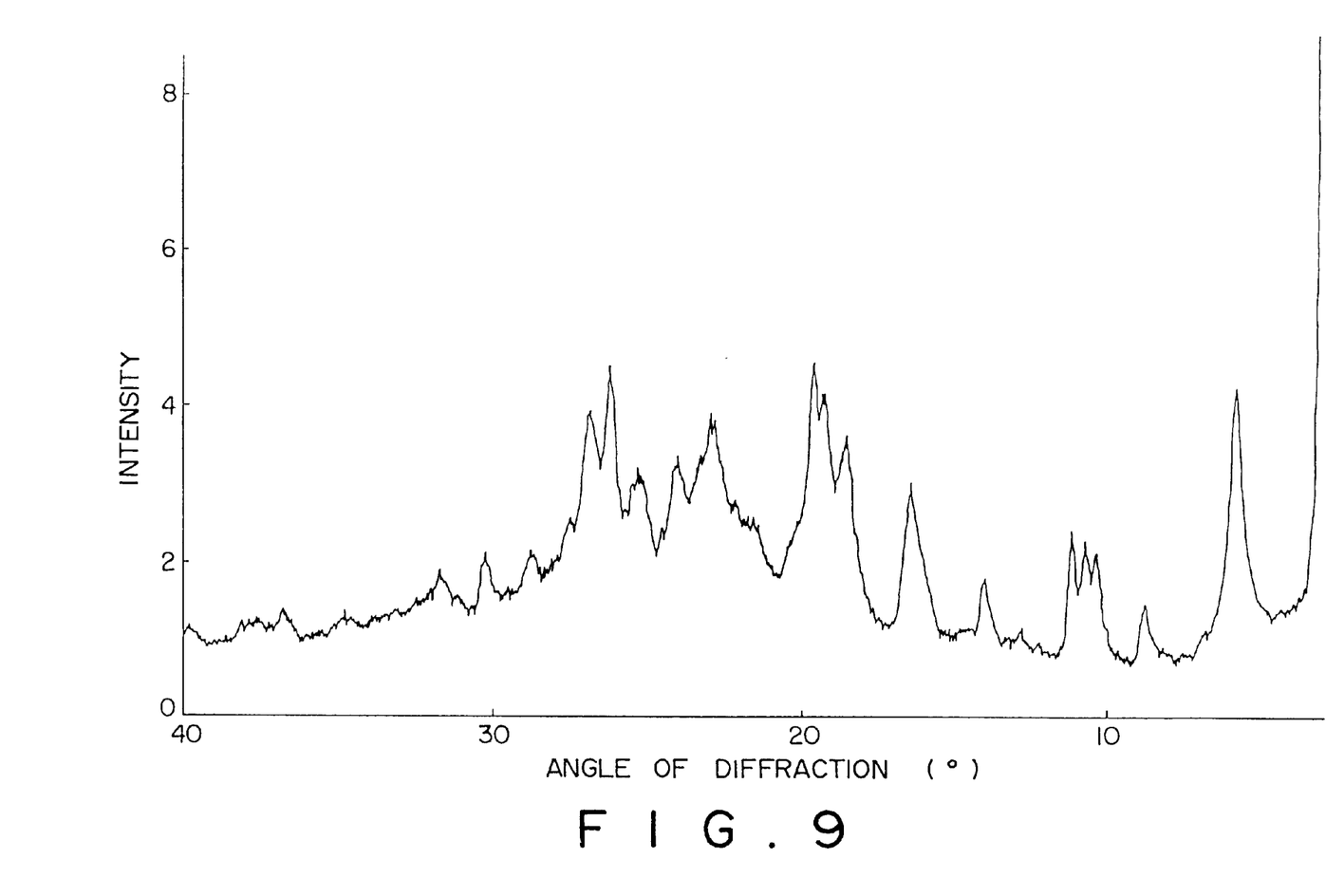
FIG. 9 is a graph showing a powder X-ray diffraction spectrum of the prior art crystalline 2-octynyl adenosine monohydrate.

The properties of the prior art crystalline 2-octynyl adenosine monohydrate are as follows:

(a) Powder X-ray diffraction spectrum: As shown in FIG. 9.

Figure 10:
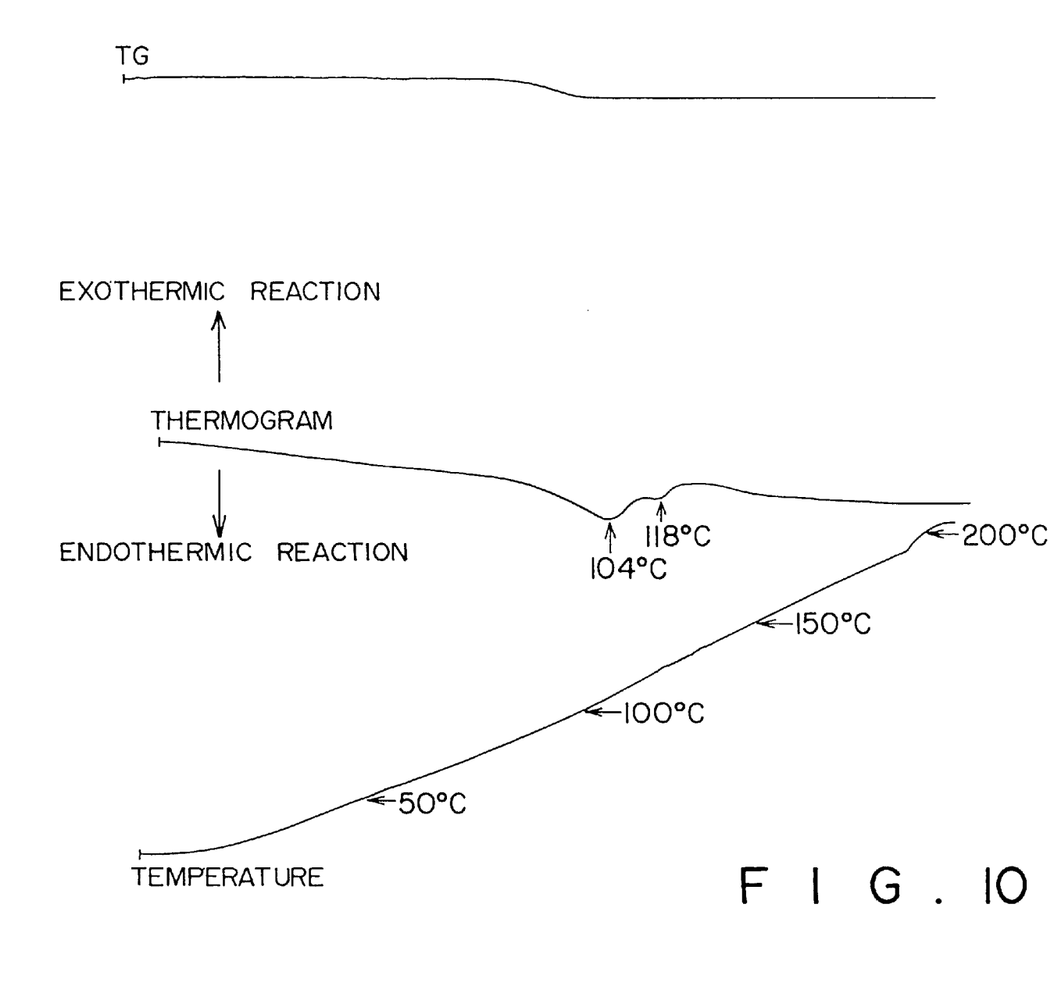
FIG. 10 is a graph showing a thermogram of the prior art crystalline 2-octynyl adenosine monohydrate.

(b) Thermogram: An endothermic reaction at 104° C. and 118° C. is observed and the curve obtained is as shown in FIG. 10.

Figure 11:
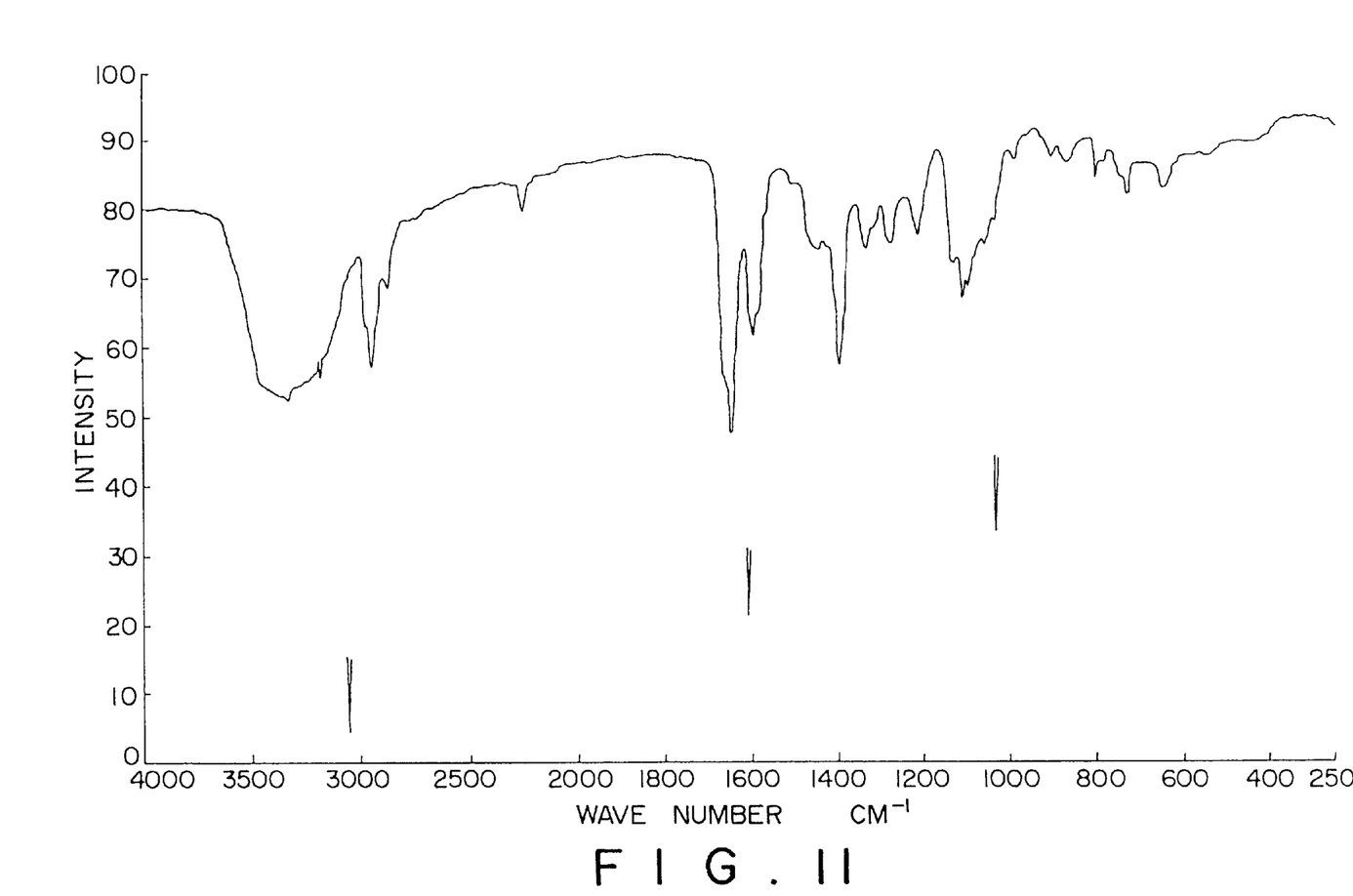
FIG. 11 is a graph showing an infrared absorption spectrum of the prior art crystalline 2-octynyl adenosine monohydrate.

(c) Infrared absorption spectrum: As shown in FIG. 11.

Figure 12:
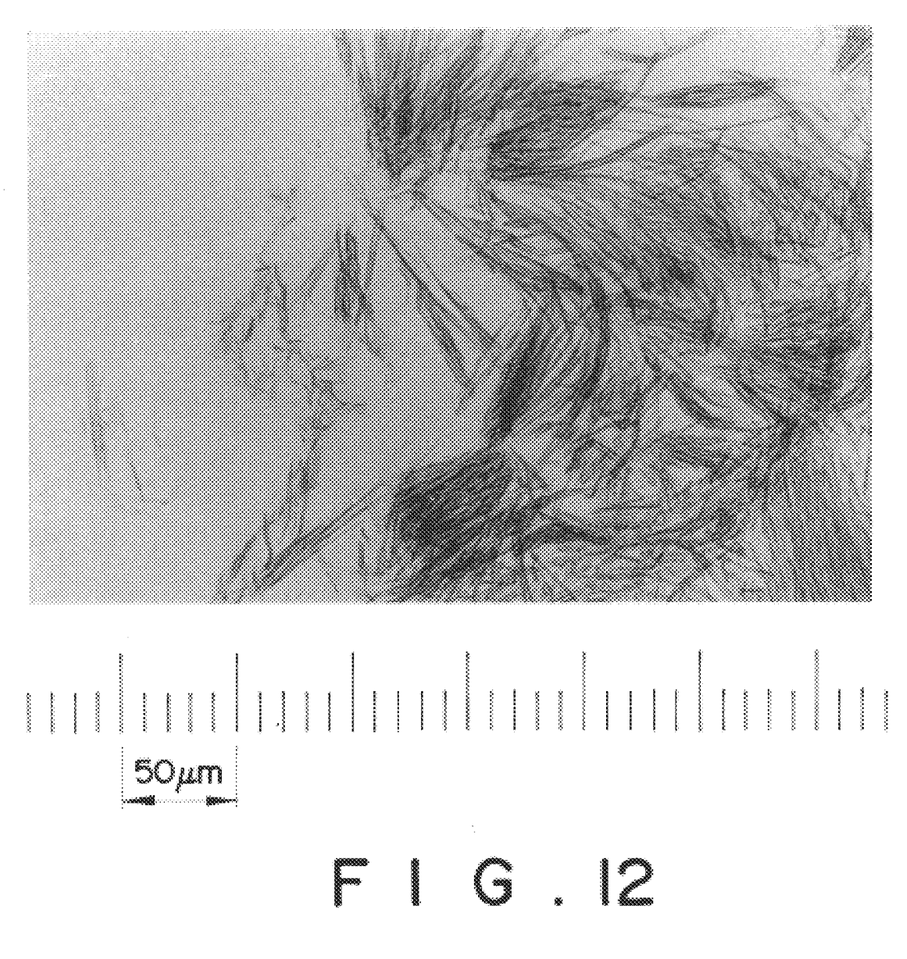
FIG. 12 is a photomicrograph showing the crystal form of the prior art crystalline 2-octynyl adenosine monohydrate (at a magnification of 330).

(d) Crystal form: As shown in FIG. 12.

The same instruments and conditions as in the case of solid 2-octynyl adenosine products of the present invention were employed in the measurements.

EXAMPLES

The following non-limiting examples are intended to illustrate the present invention more fully. All percentages herein are by weight unless otherwise indicated.

Example 1

2-Octynyl adenosine monohydrate crystal produced in accordance with the prior method was vacuum dried in the presence of phosphorus pentoxide under 5mmHg at 80° C. to produce solid 2-octynyl adenosine products having a water content of 3.14 to 0.93%.

Each product thus obtained was contained and sealed in a brown bottle wherein the relative humidity had been previously adjusted to not more than 30% by using silica gel. Each product was stored at 25° C. The results are shown in Table 3.

TABLE 3

| Product | Water Content (%) | Percentage of the Remaining Product (%) | | |
|---|---|---|---|---|
| | | At the Beginning of Storage | After 20 days | After 30 days |
| Prior art product (monohydrate crystal) | 4.56 | 100 | 82.5 | 75.9 |
| Dried product | 3.14 | 100 | 93.7 | 88.7 |
| | 2.67 | 100 | 96.9 | 97.9 |
| | 2.33 | 100 | 97.3 | 96.3 |
| | 1.73 | 100 | 98.1 | 97.0 |
| | 0.93 | 100 | 99.4 | 99.2 |

Example 2

The solid 2-octynyl adenosine having a water content of not more than 1% obtained in Example 1 was dissolved in n-propanol having the following water contents at 60° C. so that the concentration of 2-octynyl adenosine was 15% (W/V) and cooled to room temperature to separately crystallize 2-octynyl adenosine. Each of the solid 2-octynyl adenosines thus obtained was stored for 15 days at a temperature of 50° C. under a relative humidity of 57% for evaluation of its stability. The results are shown in Table 4.

TABLE 4

| Water Content of n-propanol (%) | At the Beginning of Storage | Percentage of the Remaining Product (%) | | | |
|---|---|---|---|---|---|
| | | After 1 day | After 3 days | After 6 days | After 15 days |
| 0 | 99.2 | 99.3 | 99.1 | 99.4 | 99.1 |
| 0.5 | 99.3 | 99.4 | 99.2 | 99.0 | 99.2 |
| 1 | 99.2 | 98.9 | 89.8 | 79.4 | — |
| 3 | 99.2 | 98.0 | 79.2 | 68.1 | — |
| 5 | 99.2 | 97.9 | 82.3 | 72.7 | — |
| 10 | 99.3 | 98.2 | 79.2 | 66.8 | — |

Solid 2-octynyl adenosine products of the present invention were obtained in the same manner as that described above using ethanol or n-butanol having a moisture content of less than 1%. When the solid 2-octynyl adenosine products obtained were stored under the same conditions as those described above, they all exhibited 99% or higher in respect of percentage of the remaining product.

What is claimed is:

1. Solid 2-octynyl adenosine having a water content of not more than 3%.

2. The solid 2-octynyl adenosine according to claim 1, wherein the water content is not more than 1%.

3. The solid 2-octynyl adenosine according to claim 1, which possesses the following properties:
   (a) a thermogram showing an endothermic reaction at 110° C. (±1° C.); and
   (b) improve stability with respect to temperature.

4. The solid 2-octynyl adenosine according to claim 2, which possesses the following properties:
   (a) a thermogram showing an endothermic reaction at 110° C. (±1° C.); and
   (b) improve stability with respect to temperature.

5. Solid 2-octynyl adenosine which is deposited from an anhydrous alcoholic solution or hydrous alcoholic solution of 2-octynyl adenosine, wherein said hydrous alcoholic solution contains a water content of less than 1%.

6. The solid 2-octynyl adenosine according to claim 5, which is deposited from an anhydrous alcoholic solution of 2-octynyl adenosine.

7. The solid 2-octynyl adenosine according to claim 5, which is deposited from an alcoholic solution of 2-octynyl adenosine wherein the alcohol has not more than 6 carbon atoms in the molecule.

8. The solid 2-octynyl adenosine according to claim 5, which is deposited from an alcohol selected from the group consisting of ethanol, propanol and butanol.

9. The solid 2-octynyl adenosine according to claim 5, which is deposited from an anhydrous propanol solution or hydrous propanol solution of 2-octynyl adenosine, said hydrous propanol solution having a water content of less than 1%, and possesses the following properties:
   (a) a thermogram showing an endothermic reaction at 98° C. (±1° C.); and
   (b) improve stability with respect to temperature and humidity.

10. The solid 2-octynyl adenosine according to claim 5, which is deposited from an anhydrous butanol solution or hydrous butanol solution of 2-octynyl adenosine, said hydrous butanol solution having a water content of less than 1%, and possesses the following properties:
    (a) a thermogram showing an endothermic reaction at 99° C. (±1° C.); and
    (b) improve stability to temperature and humidity.

11. The solid 2-octynyl adenosine according to claim 5, which is deposited from an anhydrous ethanol solution or hydrous ethanol solution of 2-octynyl adenosine, said hydrous ethanol solution having a water content of less than 1%, and possesses the following properties:
    (a) a thermogram showing an endothermic reaction at 110° C. (±1° C.); and
    (b) improve stability with respect to temperature and humidity.

12. Solid 2-octynyl adenosine having a water content of not more than 3% obtained by dehydrating 2-octynyl adenosine having a water content of above 3% to reduce the water content to not more than 3%.

13. The solid 2-octynyl adenosine according to claim 12 having a water content of not more than 1% obtained by carrying out the dehydration to reduce the water content to not more than 1%.

14. The solid 2-octynyl adenosine according to claim 12, obtained by carrying out the dehydration under reduced pressure at a temperature lower than the melting point of the 2-octynyl adenosine.

15. The solid 2-octynyl adenosine according to claim 12, obtained by carrying out the dehydration under reduced pressure and at a temperature of 50° to 90° C.

16. The solid 2-octynyl adenosine according to claim 12, which possesses the following properties:
    (a) a thermogram showing an endothermic reaction at 110° C. (±1° C.); and
    (b) improved stability with respect to temperature.

17. Solid 2-octynyl adenosine having a water content of not more than 3% obtained by dehydrating 2-octynyl adenosine having a water content of above 3% to reduce the water content to not more than 3%, dissolving the resultant 2-octynyl adenosine in absolute alcohol or a hydrous alcohol containing less than 1% water with heating, and thereafter cooling the solution to deposit the desired 2-octynyl adenosine.

18. The solid 2-octynyl adenosine according to claim 17 having a water content of not more than 1%, obtained by carrying out the dehydration to reduce the water content to not more than 1%.

19. The solid 2-octynyl adenosine according to claim 17, which is obtained by carrying out the dehydration under reduced pressure and at a temperature of 50° to 90° C.

20. The solid 2-octynyl adenosine according to claim 17, which is obtained by the use of an alcohol having not more than 6 carbon atoms in the molecule.

21. The solid 2-octynyl adenosine according to claim 17, which is obtained by the use of an alcohol selected from the group consisting of ethanol, propanol and butanol.

22. The solid 2-octynyl adenosine according to claim 17, which is obtained by the use of propanol as the alcohol, and possesses the following properties:

(a) a thermogram showing an endothermic reaction at 98° C. (±1° C.); and (b) improved stability with respect to temperature and humidity.

23. The solid 2-octynyl adenosine according to claim 17, which is obtained by the use of butanol as the alcohol, and possesses the following properties:

(a) a thermogram showing an endothermic reaction at 99° C. (±1° C.); and (b) improved stability with respect to temperature and humidity.

24. The solid 2-octynyl adenosine according to claim 17, which is obtained by the use of ethanol as the alcohol, and possesses the following properties:

(a) a thermogram showing an endothermic reaction at 110° C. (±1° C.); and (b) improved stability with respect to temperature and humidity.

* * * * *